United States Patent [19]
Boutelle et al.

[11] Patent Number: 5,380,267
[45] Date of Patent: Jan. 10, 1995

[54] NOISE-ATTENUATING PNEUMATIC COMPRESSOR AND MEDICAL APPARATUS INCORPORATING SAME

[75] Inventors: James E. Boutelle, Morristown; Kevin M. Carroll, Wayne; Jonathan R. Williams, Montville, all of N.J.

[73] Assignee: Datascope Investment Corp., Montvale, N.J.

[21] Appl. No.: 79,009

[22] Filed: Jun. 18, 1993

[51] Int. Cl.⁶ .............................................. A61M 1/10
[52] U.S. Cl. ....................................................... 600/18
[58] Field of Search ............................. 600/16, 17, 18

[56] References Cited

U.S. PATENT DOCUMENTS

| | | | |
|---|---|---|---|
| 3,266,487 | 8/1966 | Watkins et al. | 600/18 |
| 3,720,199 | 3/1973 | Rishton et al. | 600/18 |
| 4,571,159 | 2/1986 | Beardmore | 417/366 |
| 4,610,604 | 9/1986 | Iwamori | 417/269 |
| 4,761,119 | 8/1988 | Nomura et al. | 417/269 |
| 4,782,817 | 11/1988 | Singh et al. | 600/17 |
| 4,796,606 | 1/1989 | Mushika | 600/18 |
| 4,863,356 | 9/1989 | Ikeda et al. | 417/269 |
| 4,929,157 | 5/1990 | Steele et al. | 417/312 |
| 4,988,269 | 1/1991 | Blass | 417/312 |
| 5,022,146 | 6/1991 | Gannaway et al. | 417/313 |
| 5,022,469 | 6/1991 | Westerberg | 173/170 |
| 5,067,878 | 11/1991 | Da Costa | 417/312 |
| 5,133,647 | 7/1992 | Herron et al. | 417/312 |
| 5,173,034 | 12/1992 | Riffe | 417/312 |
| 5,180,292 | 1/1993 | Abousabha et al. | 417/312 |
| 5,186,614 | 2/1993 | Abousabha | 417/312 |

*Primary Examiner*—William E. Kamm
*Attorney, Agent, or Firm*—Lerner, David, Littenberg, Krumholz & Mentlik

[57] ABSTRACT

A pneumatic compression supplies both positive and negative pressure for operating a medical device. The pulsing sounds generated by the compressor are attenuated by connecting the inlet of the positive pressure side of the compressor and the outlet of the negative pressure side of the compressor to a common resonating chamber. A port in the resonating chamber acts as an outlet for the discharge of excess air in the chamber and an inlet for the entry of make-up air. By adjusting the diameter of the port with respect to the volume of the resonating chamber, sound attenuation can be optimized. In a compact design, the compressor housing serves as the resonating chamber.

33 Claims, 5 Drawing Sheets

NOISE-ATTENUATING PNEUMATIC COMPRESSOR AND MEDICAL APPARATUS INCORPORATING SAME

FIELD OF THE INVENTION

The present invention relates generally to compressors and more particularly to air compressors for supplying both a positive pressure and a negative pressure. Still more particularly, the invention relates to such air compressors which are useful for inflating and deflating medical devices, such as intra-aortic balloon pumps.

BACKGROUND OF THE INVENTION

Intra-aortic balloon pump therapy is frequently prescribed for patients who have suffered a heart attack or some other form of heart failure. In such therapy, a thin balloon is inserted through an artery into the aorta. The balloon is connected through a series of thin tubes to a complex apparatus which causes the balloon to inflate and deflate in time with the patient's heart beat, thereby assuming some of the load on the heart during the patient's recovery period.

Included in the complex inflation/deflation apparatus is a compressor which acts on a balloon driving mechanism to supply positive pressure for expanding the balloon during an inflation cycle and negative pressure for contracting the balloon during a deflation cycle. Such compressors conventionally include a pair of pistons which reciprocate out of phase with one another so as to supply the positive and negative pressures alternately. Thus, one reciprocating piston draws in outside air, compresses it and expels the air toward the balloon driving mechanism. The other piston draws air out from the balloon driving mechanism and expels it from the compressor to the atmosphere.

Each piston typically reciprocates in a cylinder having a valve plate which is provided with two reed valves, one controlling the flow of air into the cylinder and one controlling the flow of air out from the cylinder. During the intake stroke of a piston, the intake reed valve permits air to be drawn into the cylinder through the cylinder inlet, while the discharge reed valve prevents air from being drawn in through the cylinder outlet. Similarly, during the exhaust stroke of the piston, the discharge reed valve permits air to be expelled from the cylinder through the cylinder outlet, while the intake reed valve prevents air from being expelled through the cylinder inlet. The air flowing through the reed valves generates a sound much like the sound generated by the reed in a wind instrument, which sound is continually repeated or pulsed as a result of the reciprocating motion of the pistons. The turbulent flow of the air as it travels at high velocity into and out from the cylinders also generates acoustic noise in a pulsating fashion. As a result of the irritating pulsing noise they generate, the use of these compressors in hospital settings is undesirable.

Efforts have been made to attenuate the pulsing sound emitted by these compressors. Heretofore, such efforts typically have encompassed providing the inlet and outlet of the compressor with a dissipative muffler consisting of an enclosed chamber filled with a porous material. While such mufflers effectively attenuate very high frequencies, they have little affect on lower frequency sounds.

The use of non-dissipative mufflers for reducing sounds within a specific frequency range has long been recognized. One such muffler, a Helmholtz resonator, consists of a large gas-filled chamber having a small outlet. The resonator can be tuned to maximize the amount of attenuation by adjusting the length and diameter of the outlet with respect to the size of the chamber. Typically, rather large chambers are required in order to achieve effective low frequency attenuation. Hence, while these types of resonators are more effective than dissipative mufflers in attenuating pulsing sounds in the audible frequencies, they have received little consideration in connection with medical compressors where the ultimate size of the apparatus is a significant concern.

There therefore exists a need for improved sound attenuation in pneumatic compressors, and particularly those used to drive medical devices in a hospital setting. Preferably, these improvements can be achieved without significantly affecting the overall size of these compressors or the cost of manufacturing same.

SUMMARY OF THE INVENTION

The present invention addresses these needs by providing a compressor which achieves the sound-attenuating advantages of Helmholtz-type resonators without the size disadvantage typical of these resonators. One aspect of the present invention provides a compressor consisting of a housing, a cylindrical chamber having an open end connected in communication with an interior of the housing and a closed end, and a piston assembly disposed in the cylindrical chamber and having a piston head dividing the cylindrical chamber into a high pressure side between the piston head and the closed end and a low pressure side between the piston head and the open end. Drive means are provided to drive the piston assembly reciprocally in the cylindrical chamber between an intake position and an exhaust position. A suction aperture and a discharge aperture communicate with the high pressure side of the cylindrical chamber, the suction aperture being opened and closed by suction valve means and the discharge aperture being opened and closed by discharge valve means.

The compressor further includes a resonating chamber having an interior defining a predetermined volume. A flow path is provided between the interior of the resonating chamber and the suction aperture so that movement of the piston assembly from the exhaust position to the intake position draws a volume of air from the interior of the resonating chamber into the high pressure side of the cylindrical chamber. The discharge aperture of the compressor may be connected to a medical device so that movement of the piston assembly from the intake position to the exhaust position can expel this volume of air toward the medical device. Port means in the resonating chamber provide an air communication path of a preselected diameter between the interior of the resonating chamber and the exterior thereof.

In accordance with well-known acoustic principles, the large volume of the resonating chamber in relation to the diameter of the air communication path results in an attenuation of the pulsing sounds generated by the inlet side of the compressor. The diameter of the air communication path may be sized relative to the volume of the resonating chamber to optimize the degree of attenuation achieved. In a highly preferred embodiment, the housing of the compressor serves as the resonating chamber to provide a dramatic amount of attenuation while achieving significant space efficiencies. The compressor may further include a dissipative muffler connected to the port means to achieve further amounts of attenuation.

In another embodiment, the compressor may further include a tube having a preselected length connected to the port means. In accordance with this embodiment, the length of the tube and the diameter of the air communication path may be sized relative to one another and relative to the volume of the resonating chamber to optimize the amount of attenuation which can be achieved.

In yet another embodiment in accordance with the present invention, the compressor includes a housing, at least two cylindrical chambers each having an open end connected in communication with an interior of the housing and a closed end, and a piston assembly disposed in each of the cylindrical chambers and having a piston head dividing the cylindrical chamber into a high pressure side between the piston head and the closed end and a low pressure side between the piston head and the open end.

Drive means drive the piston assemblies reciprocally in the cylindrical chambers between an intake position and an exhaust position; preferably the piston assemblies are driven out of phase with one another. The piston assemblies may include a pliant membrane connected in a central region to the piston assembly and at a periphery to the cylindrical chamber so that the membrane is deflected to either side of a fixed plane upon reciprocation of the piston assembly between the intake and exhaust positions. A suction aperture and a discharge aperture communicate with the high pressure sides of the cylindrical chambers, the suction apertures being opened and closed by suction valve means, and the discharge apertures being opened and closed by discharge valve means.

The interior of the resonating chamber in accordance with this embodiment is connected to the suction aperture communicating with the high pressure side of one of the cylindrical chambers and with the discharge aperture communicating with the high pressure side of the other cylindrical chamber. Thus, as the piston assembly in the first cylindrical chamber moves from the exhaust position to the intake position, a first volume of air is drawn from the interior of the resonating chamber into the high pressure side of the first cylindrical chamber, and as the piston assembly moves from the intake position to the exhaust position, the air is expelled therefrom toward the medical device. Similarly, movement of the piston assembly in the second cylindrical chamber from the exhaust position to the intake position draws a second volume of air away from the medical device into the high pressure side of that cylindrical chamber, and movement of the piston assembly from the intake position to the exhaust position expels the second volume of air toward the interior of the resonating chamber. In this arrangement, the resonating chamber attenuates the pulsing sounds generated on the inlet side of the first cylindrical chamber and the outlet side of the second cylindrical chamber.

Again, the resonating chamber is provided with port means for providing an air communication path between the interior of the resonating chamber and the exterior thereof, the diameter of the air communication path with respect to the volume of the resonating chamber determining the degree of attenuation which results.

In highly preferred embodiments, the compressor housing serves as the resonating chamber.

In preferred arrangements, the compressor in accordance with the present invention is used to drive a medical device in the context of an overall medical apparatus. Preferably, the medical device comprises an intra-aortic balloon pump, and the compressor provides positive air pressure for expanding the balloon during an inflation cycle and negative pressure for contracting the balloon during a deflation cycle.

BRIEF DESCRIPTION OF THE DRAWINGS

A more complete appreciation of the subject matter of the present invention and the various advantages thereof can be realized by reference to the following detailed description, in which reference is made to the accompanying drawings in which.

DETAILED DESCRIPTION OF THE PREFERRED EMBODIMENTS

Figure 1:
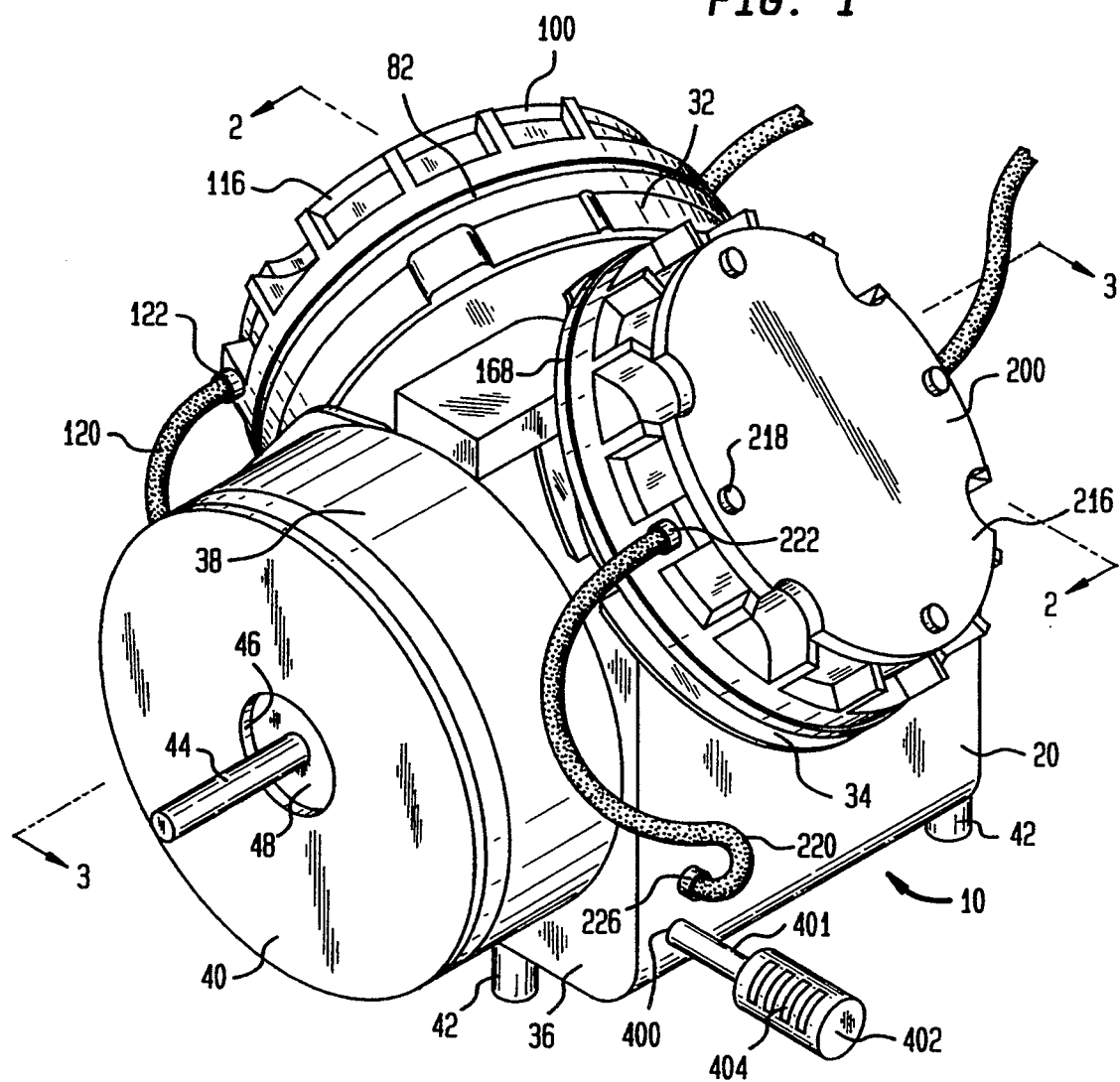
FIG. 1 is a front perspective view of one embodiment of a compressor in accordance with the present invention.
Figure 2:
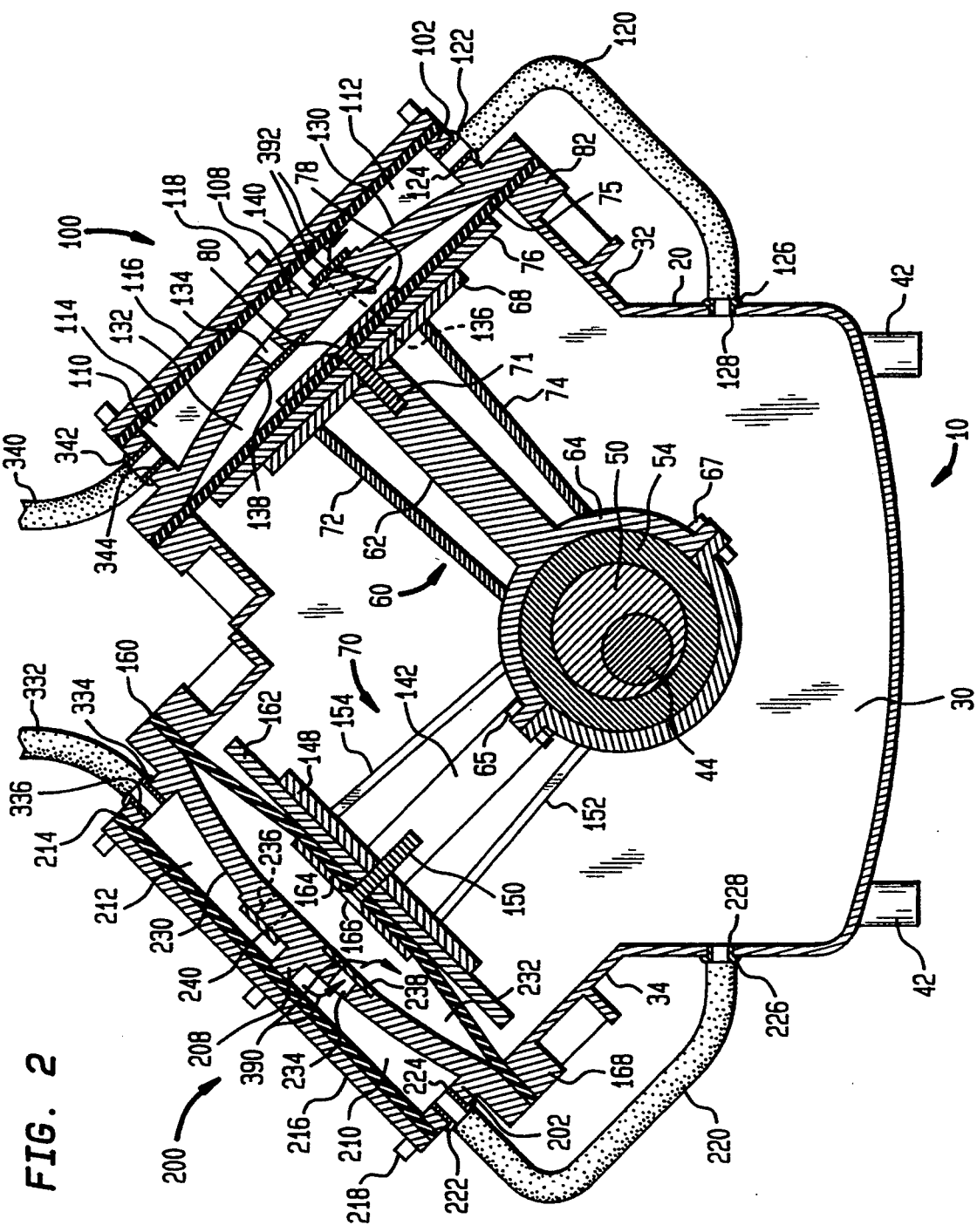
FIG. 2 is a transverse cross-sectional view taken along line 2—2 of FIG. 1.
Figure 3:
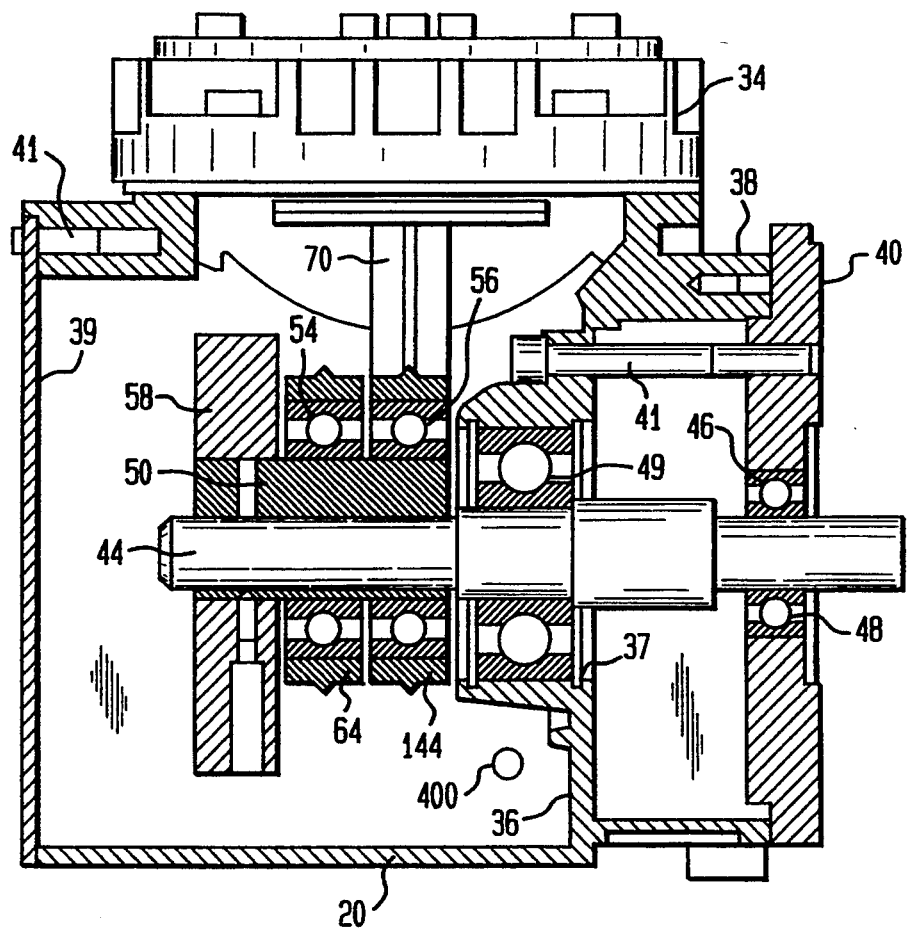
FIG. 3 is a longitudinal cross-sectional view taken along line 3—3 of FIG. 1.

Referring to FIGS. 1–3, there is illustrated a compressor 10 in accordance with one embodiment of the present invention. Compressor 10 consists of a housing 20 defining an enclosed space 30. A pair of cylindrical chambers 32 and 34 extend radially outward from the top of housing 20 defining an angle of approximately 90° therebetween. Chambers 32 and 34 are formed integrally with housing 20 such that the interior of the chambers is contiguous with enclosed space 30. The free ends of chambers 32 and 34 are enclosed by cylinder heads 100 and 200, respectively, the details of which will be described hereinbelow.

At one end, housing 20 is formed with an end wall 36 having a central opening 37. A cylindrical portion 38 extends outwardly from end wall 36 and is enclosed by a faceplate 40. A plurality of shoulder bolts 41 extend through end wall 36 and cylindrical portion 38 and threadedly engage faceplate 40 for holding faceplate 40 in assembled position. At the end opposite end wall 36, housing 20 is enclosed by a cover plate 39 secured thereto by screws 41, all of which can be seen in FIG. 3. The bottom of housing 20 and cylindrical portion 38 include internally threaded bosses 42 which enable compressor 10 to be securely mounted to a base or other support (not shown).

A rotatable drive shaft 44 is mounted axially within housing 20 and extends outwardly therefrom through central opening 37 in end wall 36 and then through an aperture 46 in faceplate 40. Drive shaft 44 is supported for rotation by a first bearing 48 arranged in aperture 46 and by a second bearing 49 arranged in central opening 37 in end wall 36. Within housing 20, a sleeve 50 is eccentrically mounted to drive shaft 44 for rotation therewith. That is, the bore 52 of sleeve 50 extends in the axial direction of the drive shaft but is offset from the central axis of the sleeve.

Sleeve 50 is fitted with a pair of bearings 54 and 56 to which a pair of piston assemblies 60 and 70 are connected for reciprocating movement in cylindrical chambers 32 and 34, respectively, upon the rotation of drive shaft 44. A counterweight 58 having a large mass is assembled to the end of drive shaft 44 to minimize any vibration in the shaft which may result from the eccentric mounting of sleeve 50.

Piston assembly 60 includes a crankshaft 62, one end of which is formed with a split collar 64 which is clamped around bearing 54 and held tightly thereground by a pair of screws 65 and 67. Bearing 54 enables drive shaft 44 and associated sleeve 50 to rotate freely with respect to piston assembly 60. At its other end, crankshaft 62 includes a support plate 68 having a centrally threaded aperture 71. A pair of struts 72 and 74 connected between split collar 64 and support plate 68 structurally reinforce piston assembly 60 and reduce the torque exerted on crankshaft 62.

A pliant membrane 75, formed from fiber-reinforced rubber or another suitably strong and pliant material, is seated across the open end of cylindrical chamber 32. A central region of membrane 75 is sandwiched between a large diameter rigid washer 76 and a smaller diameter rigid washer 78, and the entire assembly is connected by screw 80 to threaded aperture 71 in piston assembly 60. The outer periphery of membrane 75 is held in place with respect to cylindrical chamber 32 by sandwiching same between a flange 82 formed on the free end of cylindrical chamber 32 and cylinder head 100.

Cylinder head 100 includes a generally cylindrical sidewall 102 and an upstanding rib 108 which partitions cylinder head 100 into an intake chamber 110 and a discharge chamber 112. Both chambers are enclosed by a gasket 114 and an end plate 116 which are secured to cylinder head 100 by screws 118. One end of a conduit 120 is connected in flow communication with discharge chamber 112 by a fitting 122 received in threaded aperture 124 in sidewall 102. The other end of conduit 120 is connected in flow communication with the enclosed space 30 in housing 20 by a fitting 126 received in threaded aperture 128 in housing 20. Thus, conduit 120 provides a direct flow path between discharge chamber 112 and the interior of housing 20.

Sandwiched between cylinder head 100 and membrane 75 is a valve plate 130 which is spherically curved away from membrane 75 so as to define a working space 132 therebetween. Valve plate 130 includes a suction hole 134 providing communication between intake chamber 110 and working space 132, and an exhaust hole 136 providing communication between discharge chamber 112 and working space 132. Flow through suction hole 134 is controlled by a one-way reed valve 138 attached to the concave surface of valve plate 130 facing membrane 75. The reed valve 138 consists of a flat strip of a memory material, such as spring metal, which extends over suction hole 134 and is connected at one end to valve plate 130. Valve plate 130 is machined flat in the region contacted by reed valve 138 so as to present a sealing surface. As will be explained hereinbelow, reed valve 138 permits air to flow through suction hole 134 from intake chamber 110 to working space 132 during an intake stroke of piston assembly 60, but prevents air from flowing through the suction hole from working space 132 to intake chamber 110 during an exhaust stroke of piston assembly 60. The flow through exhaust hole 136 is controlled by a one-way reed valve 140 which is substantially similar to reed valve 138, but which is connected at one end to a machined region on the convex surface of valve plate 130 facing discharge chamber 112. Thus, reed valve 140 will permit flow through exhaust hole 136 from working space 132 to discharge chamber 112 during an exhaust stroke of piston assembly 60, but will prevent flow through exhaust hole 136 from discharge chamber 112 to working space 132 during an intake stroke of piston assembly 60.

Piston assembly 70 has substantially the same structure as piston assembly 60 described above. Thus, piston assembly 70 includes a crankshaft 142 having a split collar 144 formed on one end thereof and clamped around bearing 56. Bearing 56 enables drive shaft 44 and sleeve 50 to rotate together freely with respect to piston assembly 70. The other end of crankshaft 142 includes a support plate 148 having a centrally threaded aperture 150. The torque exerted on crankshaft 142 is reduced and piston assembly 70 is structurally reinforced by struts 152 and 154 connected between split collar 144 and support plate 148.

The central region of a pliant membrane 160 is sandwiched between a large diameter rigid washer 162 and a smaller diameter rigid washer 164, the entire assembly being connected by screw 166 to threaded aperture 150 in piston assembly 70. Pliant membrane 160 extends across the open end of cylindrical chamber 34 and its outer periphery is held in place with respect thereto by sandwiching same between a flange 168 on the free end of cylindrical chamber 34 and cylinder head 200.

Cylinder head 200 is also substantially similar to cylinder head 100 and includes a generally cylindrical sidewall 202 and an upstanding rib 208 which partitions cylinder head 200 into an intake chamber 210 and a discharge chamber 212. Both chambers are enclosed by a gasket 214 and an end plate 216 secured to cylinder head 200 by screws 218. One end of a conduit 220 is connected in flow communication with the interior of intake chamber 210 by a fitting 222 received in threaded aperture 224 in sidewall 202. The other end of conduit 220 is connected in flow communication with the enclosed space 30 in housing 20 by a fitting 226 received in a threaded aperture 228 in housing 20.

Sandwiched between cylinder head 200 and membrane 160 is a valve plate 230 which is spherically curved away from membrane 160 so as to define a working space 232 therebetween. Valve plate 230 includes a suction hole 234 providing communication between intake chamber 210 and working space 232, and an exhaust hole 236 providing communication between discharge chamber 212 and working space 232. Flow through suction hole 234 is controlled by a one-way reed valve 238 attached to the concave surface of valve plate 230 facing membrane 160. Reed valve 238 extends over suction hole 234 and a portion of valve plate 230 machined to form a flat sealing surface, and is connected at one end thereto. As will be explained hereinbelow, reed valve 238 permits air to flow through suction hole 234 from intake chamber 210 to working space 232 during an intake stroke of piston assembly 70, but prevents air from flowing through the suction hole from working space 232 to intake chamber 210 during an exhaust stroke of piston assembly 70. The flow through exhaust hole 236 is controlled by a one-way reed valve 240 which is connected at one end to a machined region on the convex surface of valve plate 230 facing discharge chamber 212. Thus, reed valve 240 will permit flow through exhaust hole 236 from working space 232 to discharge chamber 212 during an exhaust stroke of piston assembly 70, but will prevent flow through exhaust hole 236 from discharge chamber 212 to working space 232 during an intake stroke of piston assembly 70.

Figure 5:
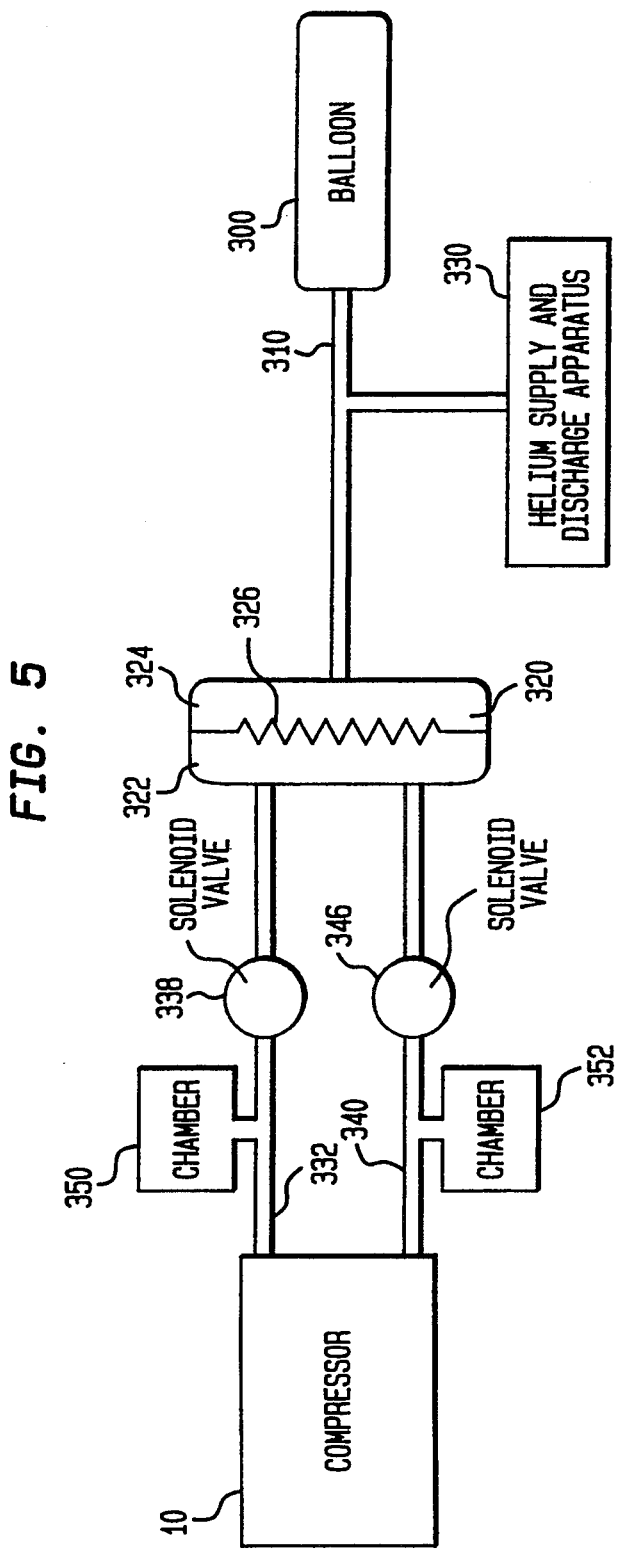
FIG. 5 is a highly schematic view showing the application of the compressor of the present invention to drive a medical device.

In a typical arrangement, compressor 10 may be part of a medical apparatus in which the compressor is used for driving a medical device, such as, for example, inflating and deflating an intra-aortic balloon pump. In one such arrangement, shown schematically in FIG. 5, a balloon 300 is surgically inserted into a patient's aorta and is connected through a thin conduit 310 to an isolator 320. Isolator 320 is divided into a primary side 322 and a secondary side 324 by a diaphragm 326, and the entire volume between diaphragm 326 and balloon 300 is typically filled with a gas, such as helium, supplied by a gas source 330. A conduit 332 is connected at one end by a fitting 334 received within threaded aperture 336 in the sidewall 202 of compressor 10 and is connected at its opposite end to the primary side 322 of isolator 320 for providing flow communication between discharge chamber 212 and isolator 320. A solenoid valve 338 controls flow through conduit 332 between discharge chamber 212 and isolator 320. A second conduit 340 is connected at one end to a fitting 342 received within a threaded aperture 344 in sidewall 102 and is connected at its opposite end to the primary side 322 of isolator 320 for providing flow communication between intake chamber 110 and isolator 320. Another solenoid valve 346 controls flow through conduit 340 between intake chamber 110 and isolator 320. A pair of enlarged chambers 350 and 352 are connected in branched relationship to conduits 332 and 340, respectively, to attenuate the sound generated by the air flow between the compressor and the isolator, as explained more fully below.

A very simplified explanation of the conventional operation of the medical apparatus will now be provided. Drive shaft 44 is rotated by a power source which is typically in the form of a DC motor (not shown). As drive shaft 44 rotates, the eccentric connection of sleeve 50 to the drive shaft causes piston assemblies 60 and 70 to reciprocate within their respective cylindrical chambers. Thus, as piston assembly 70 moves from an exhaust position in which membrane 160 is deflected toward valve plate 230 to an intake position in which membrane 160 is deflected away from valve plate 230, a pressure decrease will be created in working space 232. When there is a sufficient difference between the pressure in intake chamber 210 and the pressure in working space 232, reed valve 238 will be deflected away from suction hole 234 and air will be drawn rapidly from the enclosed space 30 in housing 20 through conduit 220 and into intake chamber 210. The air will then be drawn through suction hole 234 into working space 232, as shown by arrows 390. Reed valve 240 will prevent air from flowing through exhaust hole 236 from discharge chamber 212 into working space 232. Continued rotation of shaft 44 will cause piston assembly 70 to move from the intake position back to the exhaust position. As membrane 160 moves toward valve plate 230, the air within working space 232 will be compressed until there is a sufficient difference between the pressure in working space 232 and the pressure in discharge chamber 212. At this point, reed valve 240 will be deflected away from exhaust hole 236 and the air will flow rapidly through exhaust hole 236 from working space 232 into discharge chamber 212 and then out through conduit 332 toward valve 338. Reed valve 238 will prevent the air from flowing back out through suction hole 234 from working space 232 to intake chamber 210. The rapid and turbulent movement of air as it travels in pulses into and out from cylinder head 200 generates pulses of a very audible "rushing" sound. Additional pulsing sounds are generated by the movement of the air in repeated spurts across reed valves 238 and 240.

During the time that piston assembly 70 is reciprocating in cylindrical chamber 34, piston assembly 60 is reciprocating in a similar fashion in cylindrical chamber 32. However, since the piston assemblies are mounted at different radial angles on sleeve 50, piston assemblies 60 and 70 will reciprocate out of phase with one another. Typically, the phase difference between the reciprocation of piston assemblies 60 and 70 will be about 90°, although, where desirable, the phase differences may be other than 90°.

As drive shaft 44 is rotated, piston assembly 60 will move from an exhaust position in which membrane 75 is deflected toward valve plate 130 to an intake position in which membrane 75 is deflected away from valve plate 130. This movement of membrane 75 will cause a pressure decrease within working space 132. When a sufficient difference develops between the pressure in working space 132 and the pressure in intake chamber 110, reed valve 138 will be deflected away from suction hole 134 and air will be drawn rapidly away from valve 346 through conduit 340 and into intake chamber 110. This air will then be drawn through suction hole 134 and into working space 132. Reed valve 140 will prevent air from flowing through exhaust hole 136 from discharge chamber 112 to working space 132. Continued rotation of drive shaft 44 will move piston assembly 60 toward the exhaust position and cause membrane 75 to deflect toward valve plate 130. As membrane 75 is deflected, the air within working space 132 will be compressed until there is a sufficient difference between the pressure in working space 132 and the pressure in discharge chamber 112. At this point, reed valve 140 will be deflected away from exhaust hole 136, permitting the compressed air within working space 132 to flow quickly through exhaust hole 136 to discharge chamber 112, as shown by arrows 392, and then out therefrom through conduit 120 into the enclosed space 30 within housing 20. Again, audible pulsing sounds result from the rapid and turbulent movement of air into and out from cylinder head 100 and across reed valves 138 and 140.

During its operation, the medical device is driven by both positive pressure flow emanating from cylinder head 200 and negative pressure flow emanating from cylinder head 100, which flows are not necessarily in equilibrium. Thus, the conditions of operation of the medical apparatus may be such that more air is drawn out of the enclosed space 30 in housing 20 by operation of piston assembly 70 than is supplied thereto by operation of piston assembly 60, whereby a negative pressure will develop in housing 20 such that there is insufficient air available to create the positive pressure needed to inflate balloon 300. In that event, the negative pressure within housing 20 will cause makeup air to flow through a port 400 from outside of housing 20 to the enclosed space 30 within the housing. On the contrary, the conditions of operation may be such that piston assembly 60 supplies more air to the enclosed space 30 within housing 20 than is withdrawn therefrom by piston assembly 70, causing a positive pressure to develop within the enclosed space 30 in housing 20. In that case, this positive pressure may be expelled from enclosed space 30 through port 400.

In the embodiment described above, housing 20 acts as a Helmholtz resonator to attenuate the pulsing sounds generated at the inlet to cylinder head 200 and the outlet from cylinder head 100 so long as the dimensions of the housing are smaller than the wavelength of the sound. In accordance with well-known principles of sound attenuation, the relative diameter of port 400 with respect to the volume of the enclosed space 30 in housing 20 determines the attenuation versus frequency characteristic of the resonator. As is also well-known, an elongated tube 401 optionally may be assembled to port 400, wherein the length of the tube 401 influences the amount of attenuation which can be achieved. Thus, by appropriately sizing port 400 and tube 401, the amount of attenuation can be optimized. Where a further degree of attenuation is desirable, a conventional type of dissipative muffler 402 filled with a porous material 404 may be assembled to the end of tube 401.

The pulsing sounds generated by the flow of air between cylinder head 200 and isolator 320, and between isolator 320 and cylinder head 100, may be attenuated by enlarged chambers 350 and 352, respectively. That is, chambers 350 and 352 also act as Helmholtz resonators and can thus be sized independently to optimize the amount of attenuation. It will be appreciated that a single enlarged chamber cannot be connected between conduits 332 and 340 since such arrangement would result in circular flow which will travel into and out from compressor 100 and which will never reach isolator 320.

Figure 4:
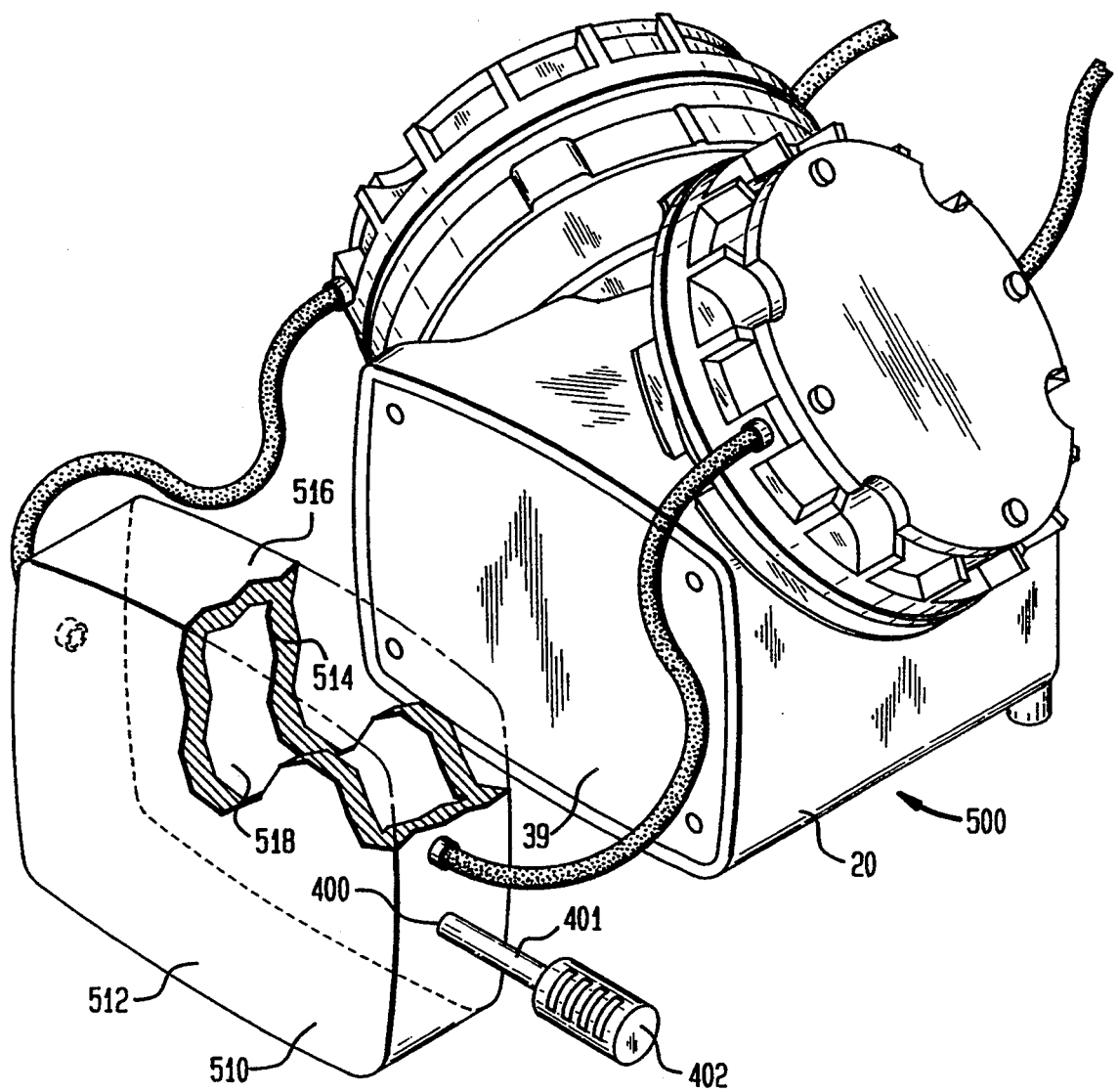
FIG. 4 is a rear perspective view of a second embodiment of a compressor in accordance with the present invention.

The compressor 10 described above provides sound attenuation in a compact size by taking advantage of the enclosed space within housing 20. In a less preferred embodiment depicted in FIG. 4, the pulsing sound generated by a compressor 500 having substantially the same construction as compressor 10 may be attenuated by connecting the intake chamber 210 and the discharge chamber 112 of the compressor to a separate resonating chamber 510. Thus, resonating chamber 510 may include a front wall 512, a rear wall 514 and a peripheral wall 516 defining a completely enclosed space 518, and may be assembled to housing 20 over cover plate 39. Indeed, if formed with an appropriate profile, resonating chamber 510 can take the place of cover plate 39 to enclose the open end of housing 20. When a separate resonating chamber 510 defining its own enclosed space is assembled to housing 20, port 400 is provided in the resonating chamber to provide communication between the enclosed space and the atmosphere, and an elongated tube 401 and a dissipative muffler 402 may optionally be connected thereto.

The separate resonating chamber 510 may also be connected to compressor 500 in such manner as to provide two resonating chambers in series. In such arrangement, both the intake chamber 210 and the discharge chamber 112 of the compressor may be connected either to the resonating chamber 510 or to the housing 20 to effect two coupled resonators. Flow communication between the enclosed space 30 in housing 20 and the enclosed space 518 in resonating chamber 510 may be provided by a port (not shown) extending between these spaces. Where intake chamber 210 and discharge chamber 112 are connected to housing 20, port 400 is preferably located in resonating chamber 510. To the contrary, where intake chamber 210 and discharge chamber 112 are connected to resonating chamber 510, port 400 is preferably located in housing 20. Both housing 20 and resonating chamber 510 could then provide sound attenuation, and each can be separately tuned to optimize the results.

Alternatively, resonating chamber 510 may be formed with a peripheral wall 516 and a front wall 512, but without a rear wall 514. In such embodiment, resonating chamber 510 may be assembled to housing 20 to increase the volume of enclosed space 30 therein to achieve further attenuating capabilities. These embodiments including a resonating chamber 510 assembled to housing 20 are less preferred because such assembly will have the undesirable affect of increasing the overall size of the compressor.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as set forth in the appended claims.

We claim:
1. A compressor, comprising
a housing having an interior defining an enclosed space,
a cylindrical chamber having an open end connected in communication with an said interior of said housing and a closed end,
a piston assembly disposed in said cylindrical chamber and having a piston head dividing said cylindrical chamber into a high pressure side between said piston head and said closed end and a low pressure side between said piston head and said open end,
drive means for driving said piston assembly reciprocally in said cylindrical chamber between an intake position and an exhaust position,
a suction aperture and a discharge aperture communicating with said high pressure side of said cylindrical chamber,
suction valve means for opening and closing said suction aperture,
discharge valve means for opening and closing said discharge aperture,
a resonating chamber having an interior defining a predetermined volume and an exterior,
means for providing a flow path between said interior of said resonating chamber and said suction aperture so that movement of said piston assembly from said exhaust position to said intake position draws a volume of air from said interior of said resonating chamber into said high pressure side of said cylindrical chamber,
means for connecting said discharge aperture to an external device so that movement of said piston assembly from said intake position to said exhaust position expels said volume of air from said high pressure side of said cylindrical chamber toward the external device, and
port means in said resonating chamber for providing an air communication path of a preselected diameter between said interior of said resonating chamber and said exterior of said resonating chamber.
2. The compressor as claimed in claim 1, further comprising a dissipative muffler connected to said port means.

3. The compressor as claimed in claim 1, wherein said preselected diameter of said air communication path is sized relative to said predetermined volume of said resonating chamber to optimize the attenuation of sound emanating from the compressor.

4. The compressor as claimed in claim 1, further comprising a tube having a preselected length connected to said port means, wherein said preselected length of said tube and said preselected diameter of said air communication path are sized relative to one another and relative to said predetermined volume of said resonating chamber to optimize the attenuation of sound emanating from the compressor.

5. The compressor as claimed in claim 4, further comprising a dissipative muffler connected to an end of said tube exterior of said resonating chamber.

6. The compressor as claimed in claim 1, further comprising means for connecting the external device to said interior of said resonating chamber independently of said discharge aperture.

7. The compressor as claimed in claim 1, wherein said interior of said housing comprises said resonating chamber of said predetermined volume.

8. A compressor, comprising
a housing having an interior defining an enclosed space,
at least two cylindrical chambers, said cylindrical chambers each having an open end connected in communication with said interior of said housing and a closed end,
a piston assembly disposed in each said cylindrical chamber and having a piston head dividing said cylindrical chamber into a high pressure side between said piston head and said closed end and a low pressure side between said piston head and said open end,
drive means for driving said piston assemblies reciprocally in said cylindrical chambers between an intake position and an exhaust position,
a suction aperture and a discharge aperture communicating with said high pressure sides of said cylindrical chambers,
suction valve means for opening and closing said suction apertures,
discharge valve means for opening and closing said discharge apertures,
a resonating chamber having an interior defining a predetermined volume and an exterior,
means for providing a flow path between said interior of said resonating chamber and said suction aperture communicating with said high pressure side of one of said cylindrical chambers so that movement of said piston assembly in said one of said cylindrical chambers from said exhaust position to said intake position draws a first volume of air from said interior of said resonating chamber into said high pressure side of said one of said cylindrical chambers,
means for connecting said discharge aperture communicating with said high pressure side of said one of said cylindrical chambers to an external device so that movement of said piston assembly in said one of said cylindrical chambers from said intake position to said exhaust position expels said first volume of air from said high pressure side of said one of said cylindrical chambers toward the external device,
means for connecting the external device to said suction aperture communicating with said high pressure side of another of said cylindrical chambers so that movement of said piston assembly in said another of said cylindrical chambers from said exhaust position to said intake position draws a second volume of air away from the external device into said high pressure side of said another of said cylindrical chambers,
means for providing a flow path between said discharge aperture communicating with said high pressure side of said another of said cylindrical chambers and said interior of said resonating chamber so that movement of said piston assembly in said another of said cylindrical chambers from said intake position to said exhaust position expels said second volume of air from said high pressure side of said another of said cylindrical chambers toward said interior of said resonating chamber, and
port means in said resonating chamber for providing an air communication path of a preselected diameter between said interior of said resonating chamber and said exterior of said resonating chamber.

9. The compressor as claimed in claim 8, further comprising a dissipative muffler connected to said port means.

10. The compressor as claimed in claim 8, wherein said drive means includes means for driving said piston assembly in said one of said cylindrical chambers out of phase with said piston assembly in said another of said cylindrical chambers.

11. The compressor as claimed in claim 8, wherein each of said piston assemblies includes a pliant membrane connected in a central region to said piston assembly and connected at a periphery to said cylindrical chamber so that said membrane is deflected to either side of a fixed plane upon reciprocation of said piston assembly between said intake and exhaust positions.

12. The compressor as claimed in claim 8, wherein said preselected diameter of said air communication path is sized relative to said predetermined volume of said resonating chamber to optimize the attenuation of sound emanating from the compressor.

13. The compressor as claimed in claim 8, further comprising a tube having a preselected length connected to said port means, wherein said preselected length of said tube and said preselected diameter of said air communication path are sized relative to one another and relative to said predetermined volume of said resonating chamber to optimize the attenuation of sound emanating from the compressor.

14. The compressor as claimed in claim 13, further comprising a dissipative muffler connected to an end of said tube exterior of said resonating chamber.

15. The compressor as claimed in claim 8, wherein said interior of said housing comprises said resonating chamber of said predetermined volume.

16. The compressor as claimed in claim 8, wherein said resonating chamber comprises at least two resonating compartments connected in series and means for providing a flow path between said at least two resonating compartments, said interior of said housing comprising one of said resonating compartments.

17. A medical apparatus, comprising
a compressor including a housing having an interior defining an enclosed space, a cylindrical chamber having an open end connected in communication with said interior of said housing and a closed end, a piston assembly disposed in said cylindrical chamber and having a piston head dividing said cylindrical chamber into a high pressure side between said piston head and said closed end and a low pressure side between said piston head and said open end, drive means for driving said piston assembly reciprocally in said cylindrical chamber between an intake position and an exhaust position, a suction aperture and a discharge aperture communicating with said high pressure side of said cylindrical chamber, suction valve means for opening and closing said suction aperture, discharge valve means for opening and closing said discharge aperture, a resonating chamber having an interior defining a predetermined volume and an exterior, means for providing a flow path between said interior of said resonating chamber and said suction aperture so that movement of said piston assembly from said exhaust position to said intake position draws a volume of air from said interior of said resonating chamber into said high pressure side of said cylindrical chamber, and port means in said resonating chamber for providing an air communication path of a preselected diameter between said interior of said resonating chamber and said exterior of said resonating chamber, a medical device having an air inlet and an air outlet, and means for connecting said discharge aperture to said air inlet of said medical device so that movement of said piston assembly from said intake position to said exhaust position expels said volume of air from said high pressure side of said cylindrical chamber into said air inlet of said medical device.

18. The medical apparatus as claimed in claim 17, further comprising a dissipative muffler connected to said port means.

19. The medical apparatus as claimed in claim 17, wherein said preselected diameter of said air communication path is sized relative to said predetermined volume of said resonating chamber to optimize the attenuation of sound emanating from said compressor.

20. The medical apparatus as claimed in claim 17, further comprising a tube having a preselected length connected to said port means, wherein said preselected length of said tube and said preselected diameter of said air communication path are sized relative to one another and relative to said predetermined volume of said resonating chamber to optimize the attenuation of sound emanating from said compressor.

21. The medical apparatus as claimed in claim 20, further comprising a dissipative muffler connected to an end of said tube exterior of said resonating chamber.

22. The medical apparatus as claimed in claim 17, wherein said interior of said housing comprises said resonating chamber of said predetermined volume.

23. The medical apparatus as claimed in claim 17, wherein said medical device comprises an intra-aortic balloon pump.

24. A medical apparatus, comprising a compressor including a housing having an interior defining an enclosed space, at least two cylindrical chambers, said cylindrical chambers each having an open end connected in communication with said interior of said housing and a closed end, a piston assembly disposed in each said cylindrical chamber and having a piston head dividing said cylindrical chamber into a high pressure side between said piston head and said closed end and a low pressure side between said piston head and said open end, drive means for driving said piston assemblies reciprocally in said cylindrical chambers between an intake position and an exhaust position, a suction aperture and a discharge aperture communicating with said high pressure sides of said cylindrical chambers, suction valve means for opening and closing said suction apertures, discharge valve means for opening and closing said discharge apertures, a resonating chamber having an interior defining a predetermined volume and an exterior, means for providing a flow path between said interior of said resonating chamber and said suction aperture communicating with said high pressure side of one of said cylindrical chambers so that movement of said piston assembly in said one of said cylindrical chambers from said exhaust position to said intake position draws a first volume of air from said interior of said resonating chamber into said high pressure side of said one of said cylindrical chambers, means for providing a flow path between said discharge aperture communicating with said high pressure side of another of said cylindrical chambers and said interior of said resonating chamber so that movement of said piston assembly in said another of said cylindrical chambers from said intake position to said exhaust position expels said second volume of air from said high pressure side of said another of said cylindrical chambers toward said interior of said resonating chamber, and port means in said resonating chamber for providing an air communication path of a preselected diameter between said interior of said resonating chamber and said exterior of said resonating chamber, a medical device having an air inlet and an air outlet, said medical device being movable between an expanded condition and a contracted condition, means for connecting said discharge aperture communicating with said high pressure side of said one of said cylindrical chambers to said air inlet of said medical device so that movement of said piston assembly in said one of said cylindrical chambers from said intake position to said exhaust position expels said first volume of air from said high pressure side of said one of said cylindrical chambers into said air inlet of said medical device for placing said medical device in said expanded condition, and a means for connecting said air outlet of said medical device to said suction aperture communicating with said high pressure side of said another of said cylindrical chambers so that movement of said piston assembly in said another of said cylindrical chambers from said exhaust position to said intake position draws a second volume of air out from said air outlet of said medical device and into said high pressure side of said one of said cylindrical chambers for placing said medical device in said contracted condition.

25. The medical apparatus as claimed in claim 24, further comprising a dissipative muffler connected to said port means.

26. The medical apparatus as claimed in claim 24, wherein said drive means includes means for driving said piston assembly in said one of said cylindrical chambers out of phase with said piston assembly in said another of said cylindrical chambers.

27. The medical apparatus as claimed in claim 24, wherein each of said piston assemblies includes a pliant membrane connected in a central region to said piston assembly and connected at a periphery to said cylindrical chamber so that said membrane is deflected to either side of a fixed plane upon reciprocation of said piston assembly between said intake and exhaust positions.

28. The medical apparatus as claimed in claim 24, wherein said preselected diameter of said air communication path is sized relative to said predetermined volume of said resonating chamber to optimize the attenuation of sound emanating from said compressor.

29. The medical apparatus as claimed in claim 24, further comprising a tube having a preselected length connected to said port means, wherein said preselected length of said tube and said preselected diameter of said air communication path are sized relative to one another and relative to said predetermined volume of said resonating chamber to optimize the attenuation of sound emanating from said compressor.

30. The medical apparatus as claimed in claim 29, further comprising a dissipative muffler connected to an end of said tube exterior of said resonating chamber.

31. The medical apparatus as claimed in claim 24, wherein said interior of said housing comprises said resonating chamber of said predetermined volume.

32. The medical apparatus as claimed in claim 24, wherein said resonating chamber comprises at least two resonating compartments connected in series and means for providing flow communication between said at least two resonating compartments, said interior of said housing comprising one of said resonating compartments.

33. The medical apparatus as claimed in claim 24, wherein said medical device comprises an intra-aortic balloon pump.

* * * * *

UNITED STATES PATENT AND TRADEMARK OFFICE
CERTIFICATE OF CORRECTION

PATENT NO. : 5,380,267

DATED : January 10, 1995

INVENTOR(S) : Boutelle et al.

It is certified that error appears in the above-identified patent and that said Letters Patent is hereby corrected as shown below:

Column 10, line 30, "with an said" should read --with said--.

Signed and Sealed this

Twenty-fifth Day of April, 1995

Attest:

BRUCE LEHMAN

*Attesting Officer*  *Commissioner of Patents and Trademarks*